(12) United States Patent
Takahashi et al.

(10) Patent No.: US 7,436,924 B2
(45) Date of Patent: Oct. 14, 2008

(54) DATA MANAGING SYSTEM, X-RAY COMPUTED TOMOGRAPHIC APPARATUS, AND X-RAY COMPUTED TOMOGRAPHIC SYSTEM

(75) Inventors: Masashi Takahashi, Nasu-gun (JP); Satoru Shimanishi, Otawara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 308 days.

(21) Appl. No.: 10/722,417

(22) Filed: Nov. 28, 2003

(65) Prior Publication Data
US 2004/0116797 A1 Jun. 17, 2004

(30) Foreign Application Priority Data
Nov. 29, 2002 (JP) ............................. 2002-348931

(51) Int. Cl.
*A61B 6/03* (2006.01)
(52) U.S. Cl. .......................................... 378/4; 378/901
(58) Field of Classification Search ............... 378/4–20, 378/210, 901; 707/104.1
See application file for complete search history.

(56) References Cited

U.S. PATENT DOCUMENTS

| | | | |
|---|---|---|---|
| 5,430,783 A * | 7/1995 | Hu et al. ........................ 378/15 |
| 5,751,837 A * | 5/1998 | Watanabe et al. ............ 382/131 |
| 6,141,398 A * | 10/2000 | He et al. ........................ 378/4 |
| 6,389,096 B1 * | 5/2002 | Hoffman et al. .............. 378/19 |
| 6,522,714 B1 * | 2/2003 | Wang et al. ................... 378/15 |
| 6,553,248 B1 * | 4/2003 | Gagnon et al. ............... 600/407 |
| 6,658,082 B2 * | 12/2003 | Okumura et al. ............... 378/19 |
| 6,907,099 B2 * | 6/2005 | Kling et al. ..................... 378/4 |
| 2002/0029264 A1 * | 3/2002 | Ogino et al. ................. 709/223 |
| 2003/0083568 A1 * | 5/2003 | Frigo et al. .................. 600/410 |
| 2004/0019275 A1 * | 1/2004 | Iatoru et al. ................. 600/428 |

FOREIGN PATENT DOCUMENTS

JP 8-263570 10/1996
JP 9-220199 8/1997

OTHER PUBLICATIONS

Lee et al., The Optimization of Scan Timing for Contrast-Enhanced Magnetic Resonance Angiography, Korean Journal of Radiology, vol. 1, No. 3, p. 142-151, Sep. 2000).*
Turbell, Cone-Beam Reconstruction Using Filtered Backprojection, Feb. 2001, Linkoping Studies in Science and Technology dissertation No. 672.*
Flohr et al., New technical developments in multislice CT, Part 1: Approaching isotropic resolution with sub-millimeter 16-slice scanning, Jul. 2002, Fortschr Rontgenstr, vol. 174, No. 7, pp. 839-845.*

* cited by examiner

*Primary Examiner*—Edward J Glick
*Assistant Examiner*—John M Corbett
(74) *Attorney, Agent, or Firm*—Oblon, Spivak, McClelland, Maier & Neustadt, P.C.

(57) ABSTRACT

A data managing system that collectively manages raw data obtained in any of X-ray CT apparatuses with the use of a network. Raw data transmitted from any of the X-ray CT apparatuses is stored in the data managing system, and baked up to various kinds of storage devices. Also, the raw data managed by the data managing system is transmitted, at a request, to an arbitrary X-ray CT apparatus at arbitrary timing to be reconstructed therein.

13 Claims, 11 Drawing Sheets

FIG. 5

| MANAGEMENT NUMBER | NAME OF PATIENT | DATE OF PHOTOGRAPHING | DAS ARRAY NUMBER | PHOTOGRAPHING SLICE WIDTH | BACKUP STORAGE DEVICE |
|---|---|---|---|---|---|
| 012345 | TARO TOKYO | '02. 11. 26 AM10:11 | 4 | 1.0mm x 4 SLICES | SAN |
| 012566 | HANAKO OSAKA | '02. 11. 26 AM3:54 | 8 | 0.5mm x 8 SLICES | NAS |
| 012787 | ISHIRO NASU | '02. 11. 27 AM9:1 | 16 | 0.5mm x 16 SLICES | HD |
| ...... | ...... | ...... | ...... | ...... | ...... |

FIG. 8

| DAS ARRAYS SLICE WIDTH (mm) | CTB 4 (FAN BEAM RECONSTRUCTION) | CTC 8 (FAN BEAM RECONSTRUCTION) | 16 (CONE BEAM RECONSTRUCTION) |
|---|---|---|---|
| 0.5 | O | X | X |
| 1 | O | X | X |
| 2 | O | X | X |
| 3 | O | X | X |

CTA

US 7,436,924 B2

DATA MANAGING SYSTEM, X-RAY COMPUTED TOMOGRAPHIC APPARATUS, AND X-RAY COMPUTED TOMOGRAPHIC SYSTEM

CROSS-REFERENCE TO RELATED APPLICATIONS

This application is based upon and claims the benefit of priority from the prior Japanese Patent Application No. 2002-348931, filed Nov. 29, 2002, the entire contents of which are incorporated herein by reference.

BACKGROUND OF THE INVENTION

1. Field of the Invention

The present invention relates to management of projection data, such as raw data generated in modality, and more particularly to a data managing system that manages raw data generated in an X-ray computed tomographic apparatus (hereinafter, referred to as the X-ray CT apparatus), an X-ray CT apparatus, and an X-ray CT system.

2. Description of the Related Art

In the field of medical imaging, there are various kinds of modality, including X-rays, ultrasound, CT, magnetic resonance imaging (MRI), and nuclear medicine, and each provides useful images as clinical information. Recently, together with the advancement in the respective kinds of modality, improvements in image processing techniques, speedups in computer operations, and enhancement in resolution have made it possible to produce an image of an internal structure of a human body more accurately in various forms. Meanwhile, a size of data to be handled has increased, and a major portion of the CPU operations is occupied by image processing or the like, which raises a problem that a following photographing work cannot be started until the image reconstruction is completed. Also, there is another problem that when a vast volume of data (raw data, projection data, etc.) obtained through photographing is recorded in a hard disc (hereinafter, abbreviated to HD) provided in advance to the respective kinds of modality, the recording work takes so long that efficiency of a diagnostic work is decreased. Further, because a data size of the raw data is generally larger than that of a reconstructed tomographic image while the equipped HD is also used to store various kinds of data, such as patient information and diagnostic images in the past, there arises still another problem that the HD is not large enough to record a huge volume of raw data.

Hereinafter, an X-ray CT apparatus will be described by way of example in order to explain these problems more concretely. The X-ray CT apparatus generates raw data by scanning a subject with exposure of an X-ray. The raw data thus generated is sequentially recorded and saved in an internal HD of the X-ray CT apparatus or a certain storage medium. An X-ray CT image can be obtained by reading out the raw data for reconstruction followed by certain image processing. However, because the HD stores many items of examination data, such as CT image data and patient information, in addition to the raw data, the HD is not able to save a huge volume of raw data. Moreover, when image reconstruction is performed subsequently to raw data generation, a major portion of the CPU operations is occupied by the image reconstruction processing and a following photographing work cannot be started.

In addition, a multi-slice X-ray CT apparatus has been becoming popular in recent years, through the use of which image acquisition with high accuracy within a wide range can be achieved in a short time by irradiating a cone-shaped X-ray beam to a subject and detecting X-rays having passed through the subject in a multi-array detector. When compared with a single-slice X-ray CT apparatus, photographing by the multi-slice X-ray CT apparatus generates a far larger volume of raw data, and the problems described above become more apparent.

For example, in the case of raw data generated in a multi-slice X-ray CT apparatus having a 16-array detector, a full storage capacity of a typical disc with a 4.8-GB capacity is 70 rotations at the scanning rate of 0.5 sec. on one side of an MO. However, because the maximum size of the raw data generated in the multi-slice X-ray CT apparatus having the 16-array detector is 6.4 GB, the capacity of the internal HD of the apparatus is by no means sufficient. Also, not only recording takes 30 min. or longer, but also image reconstruction requires a considerable time, which may possibly cause a decrease in the efficiency of a diagnostic work.

BRIEF SUMMARY OF THE INVENTION

The present invention has been devised in view of the foregoing problems, and therefore, has an object to provide a data managing system, an X-ray CT apparatus, and an X-ray CT system capable of improving the efficiency of a diagnostic work by efficiently managing a vast volume of data obtained through photographing.

In order to achieve the above and other objects, the present invention provides units as follows.

The present invention may provide a medical image photographing system, including: a first medical image photographing apparatus; a second medical image photographing apparatus; and a data managing system. connected to the first and second medical image photographing apparatuses via a network. The first medical image photographing apparatus includes: a photographing system to obtain photographing data related to a subject by photographing the subject under at least one photographing condition; and a transmitter to transmit, via the network to the data managing system, the photographing data and appended information, which is information included in the at least one photographing condition and needed to generate biological information related to the subject. The data managing system includes: a first receiver to receive the photographing data and the appended information; a memory to store the photographing data and the appended information received; and a second transmitter to transmit the photographing data and the appended information to the second medical image photographing apparatus. The second medical image photographing apparatus includes: a second receiver to receive the photographing data and the appended information; and a biological information generating unit to generate the biological information related to the subject, based on the photographing data and the appended information received.

The present invention may further provide an X-ray computed tomographic system, including: a first X-ray computed tomographic apparatus; a second X-ray computed tomographic apparatus; and a data managing system connected to the first and second X-ray computed tomographic apparatuses via a network. The first X-ray computed tomographic apparatus includes: an X-ray irradiating unit to irradiate an X-ray to a subject while rotating about the subject; an X-ray detecting unit having a plurality of detecting element arrays aligned in a slice direction, in each of which a plurality of detecting elements, each generating electrical charges based on an incident X-ray, are aligned in a channel direction; a data acquisition unit, having a plurality of data acquisition element arrays, to read out the electrical charges from the plurality of detecting elements by using a certain number of data acquisition element arrays among the plurality of data acquisition element arrays and generate photographing data based on the electrical charges; and a first transmission unit to transmit, via the network to the data managing system, the photographing data and appended information including the number of data acquisition element arrays used when reading out the electrical charges. The data managing system includes: a first reception unit to receive the photographing data and the appended information; a storage unit to store the photographing data and the appended information received; and a second transmission unit to transmit the photographing data and the appended information to the second X-ray computed tomographic apparatus. The second X-ray computed tomographic apparatus includes: a second reception unit to receive the photographing data and the appended information; and a reconstruction unit to perform image reconstruction based on the photographing data and the appended information received.

The present invention may further provide a data managing system connected to a first X-ray computed tomographic apparatus and a second X-ray computed tomographic apparatus via a network. The data managing system includes: a reception unit to receive, from the first X-ray computed tomographic apparatus, one of raw data and projection data obtained in the first X-ray computed tomographic apparatus and appended information including the number of data acquisition element arrays used when obtaining one of the raw data and the projection data; a storage unit to store one of the raw data and the projection data, and the appended information received; and a transmission unit to transmit one of the raw data and the projection data, and the appended information to the second X-ray computed tomographic apparatus.

The present invention may further provide an X-ray computed tomographic apparatus connected, via a network, to a data managing system managing projection data. The apparatus includes: an X-ray irradiating unit to irradiate an X-ray to a subject while rotating about the subject; an X-ray detecting unit having a plurality of detecting element arrays aligned in a slice direction, in each of which a plurality of detecting elements, each generating electrical charges based on an incident X-ray, are aligned in a channel direction; a data acquisition unit, having a plurality of data acquisition element arrays, to read the electrical charges from the plurality of detecting elements by using a certain number of data acquisition element arrays among the plurality of data acquisition element arrays and generate one of raw data and projection data based on the electrical charges; and a transmission unit to transmit, via the network to the data managing system, one of the raw data and the projection data, and appended information including the number of data acquisition element arrays used when reading out the electrical charges.

The present invention may further provide an X-ray computed tomographic apparatus connected, via a network, to a data managing system managing projection data. The apparatus includes: a reception unit to receive, from the data managing system, one of raw data and projection data obtained in an X-ray computed tomographic apparatus, and appended information including the number of data acquisition element arrays used when obtaining one of the raw data and the projection data; and a reconstruction unit to perform image reconstruction based on one of the raw data and the projection data, and the appended information received.

BRIEF DESCRIPTION OF THE SEVERAL VIEWS OF THE DRAWING

FIG. 5 is a view showing an example of a management table stored into a database (DB);

FIG. 8 is a view showing an example of a reconstruction table related to an X-ray CT apparatus stored in the DB;

DETAILED DESCRIPTION OF THE INVENTION

Figure 1:
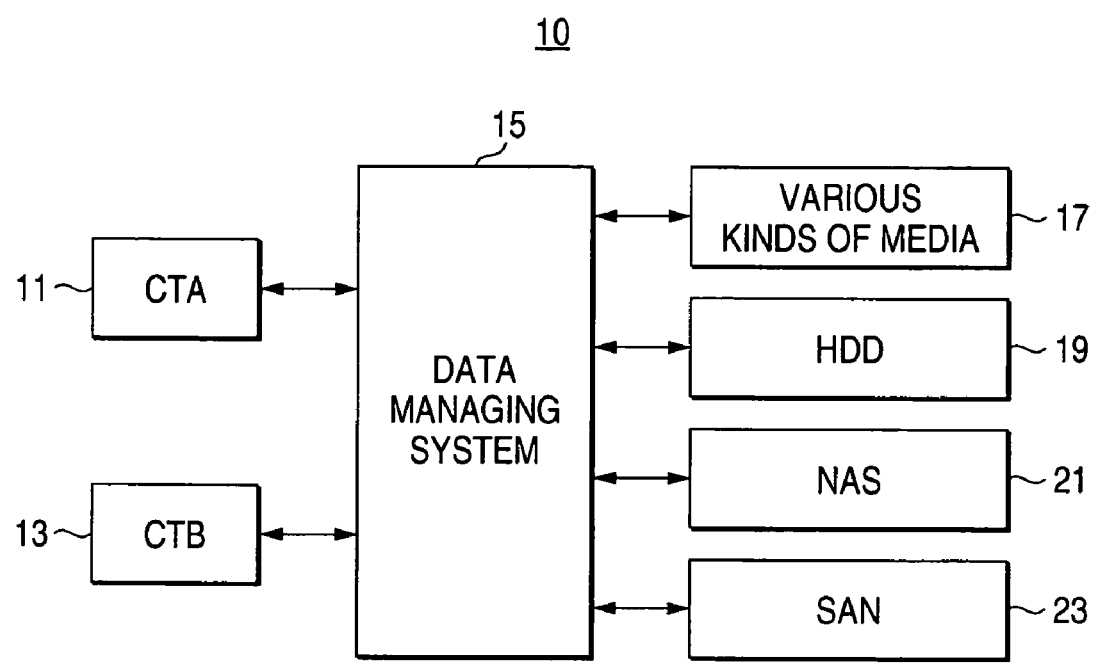
FIG. 1 is a view showing a configuration of an X-ray CT system according to one embodiment of the present invention.

First through third embodiments of the present invention will now be described with reference to the drawings. Hereinafter, components having substantially the same function and configuration are labeled with the same reference numerals, and an explanation will not be repeated unless otherwise required.

Each of the embodiments below includes a technique of sharing, within a medical institution via a network, photographing data including biological information (in particular, raw data obtained by a medial imaging apparatus, etc.), photographing information needed for subsequent generation and reproduction of the biological information (for example, image reconstruction, subsequent generation of a time intensity curve, etc.). This technique can be adapted to any kind of modality (for example, to an X-ray diagnostic apparatus, an X-ray CT apparatus, an MRI apparatus, a nuclear medical diagnostic apparatus, an ultrasonic diagnostic apparatus, etc.). In each of the embodiments below, in order to provide a concrete description, en explanation will be given to a case where an X-ray CT apparatus is chosen as the modality, and obtained raw data (or projection data) and photographing information (DAS array information) needed for subsequent image reconstruction are managed collectively and shared.

First Embodiment

FIG. 1 is a view showing a configuration of an X-ray CT system 10 according to this embodiment. As shown in FIG. 1, the X-ray CT system 10 comprises an X-ray CT apparatus A, an X-ray CT apparatus B, a data managing system 15, various kinds of media 17, an HD 18, a NAS (Network Attached Storage) 21, a SAN (Storage Area Network) 23. These components will now be described one by one.

(X-ray CT Apparatus)

Each of the X-ray CT apparatus A and the X-ray CT apparatus B is an apparatus used to obtain a tomographic image (X-ray CT image) by irradiating an X-ray to a subject and detecting an X-ray having passed through the subject followed by image reconstruction with the use of a computer. In each of the embodiments below, assume that the X-ray CT apparatus A is of a type capable of detecting 4 arrays of tomographic layers simultaneously, and the X-ray CT apparatus B is of a type capable of detecting 16 arrays of tomographic layers simultaneously, in order to provide a concrete description.

Incidentally, an X-ray CT scanner apparatus includes various types, including a ROTATE/ROTATE type in which an X-ray tube and a detector system integrally rotate about a subject, a STATIONARY/ROTATE type in which an array of a number of detecting elements are aligned ring-wise, and the X-ray tube alone rotates about the subject, a type in which the position of an X-ray source is moved electronically on the target by polarizing an electron beam, etc., and the present invention can be adapted to any of these types. Herein, an explanation will be given to an X-ray CT apparatus of the ROTATE/ROTATE type, which has now become the mainstream.

Also, in order to reconstruct one slice of tomographic data, projection data for a full circle of a subject, that is, approximately 360°, is needed, and projection data for 180° plus a view angle is needed even in the half-scan method. The technical idea of the present invention can be adapted to either method, and herein, an explanation will be given to the former typical method of reconstructing voxel data of one volume (or one tomographic image) from projection data of approximately 360°.

Figure 2:
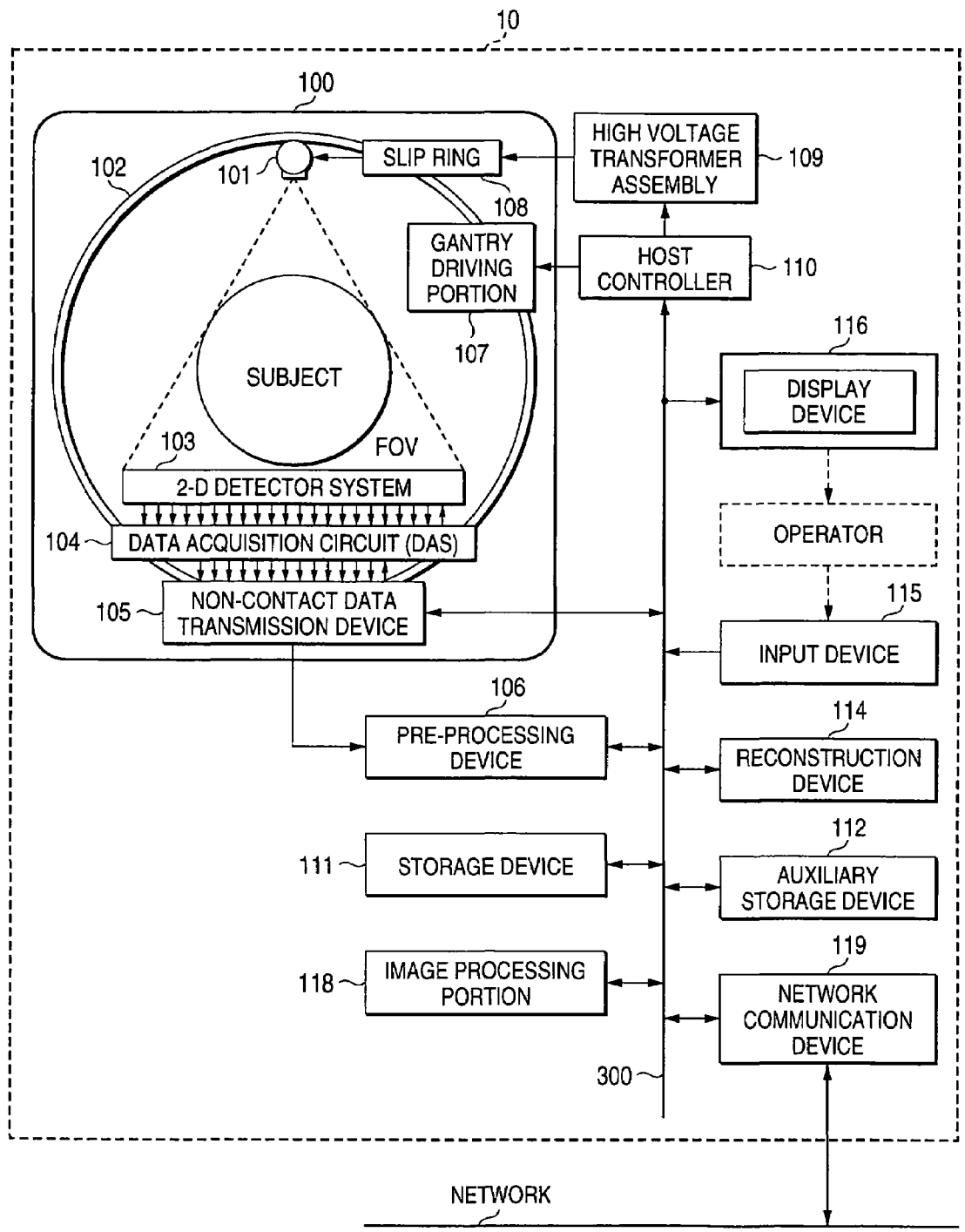
FIG. 2 is a view schematically showing a typical configuration of an X-ray CT apparatus.

FIG. 2 is a view schematically showing a typical configuration of the X-ray CT apparatuses A and B. As shown in FIG. 2, each of the X-ray CT apparatuses A and B includes an X-ray tube 101, a rotation ring 102, a 2-D detector system 103, a data acquisition circuit (DAS) 104, a non-contact data transmission device 105, a pre-processing device 106, a gantry driving portion 107, a slip ring 108, a high voltage transformer assembly 109, a host controller 110, a storage device 111, an auxiliary storage device 112, a reconstruction device 114, an input device 115, an image processing portion 118, a display device 116, and a data/control bus 300.

The X-ray tube 101 is a vacuum tube that generates an X-ray, and is provided to the rotation ring 102. Power (a tube current and a tube voltage) needed to irradiate an X-ray is supplied to the X-ray tube 101 from the high voltage transformer assembly 109 via the slip ring 108. The X-ray tube 101 irradiates an X-ray to a subject laid within a field of view FOV by accelerating electrons with a supplied high voltage to collide with the target.

Between the X-ray tube 101 and the subject is disposed a collimator (not shown) that shapes an X-ray beam irradiated from the X-ray tube 101 into a cone (prismatic cone) shape or a fan beam shape.

The rotation ring 102 is provided with the X-ray tube 101 and the detector system 103. The rotation ring 102 is driven by the gantry driving portion 107, and, together with the X-ray tube 101 and the detector system 103, rotates about a subject at a speed as high as one second or less per rotation.

The 2-D detector system 103 is a detector system that detects an X-ray having passed through the subject, and is attached to the rotation ring 102 oppositely to the X-ray tube 101. In the 2-D detector system 103 are aligned a plurality of detecting elements, each comprising a combination of a scintillator and a photodiode, in a matrix manner with respect to a body axial direction of the subject (slice direction) and a channel direction intersecting at right angles with the slice direction. Herein, for example, approximately 1,000 (1,000 channels) of detecting elements are aligned with respect to the channel direction (hereinafter, one array in which are aligned 1,000 detecting elements is referred to as "the detecting element array"). Also, in order to enlarge the field of view FOV in the body axial direction, approximately 40 detecting elements arrays are aligned with respect to the body axial direction. This configuration enables high spatial resolution to be achieved in both the channel direction and the body axial direction.

Figure 3A:
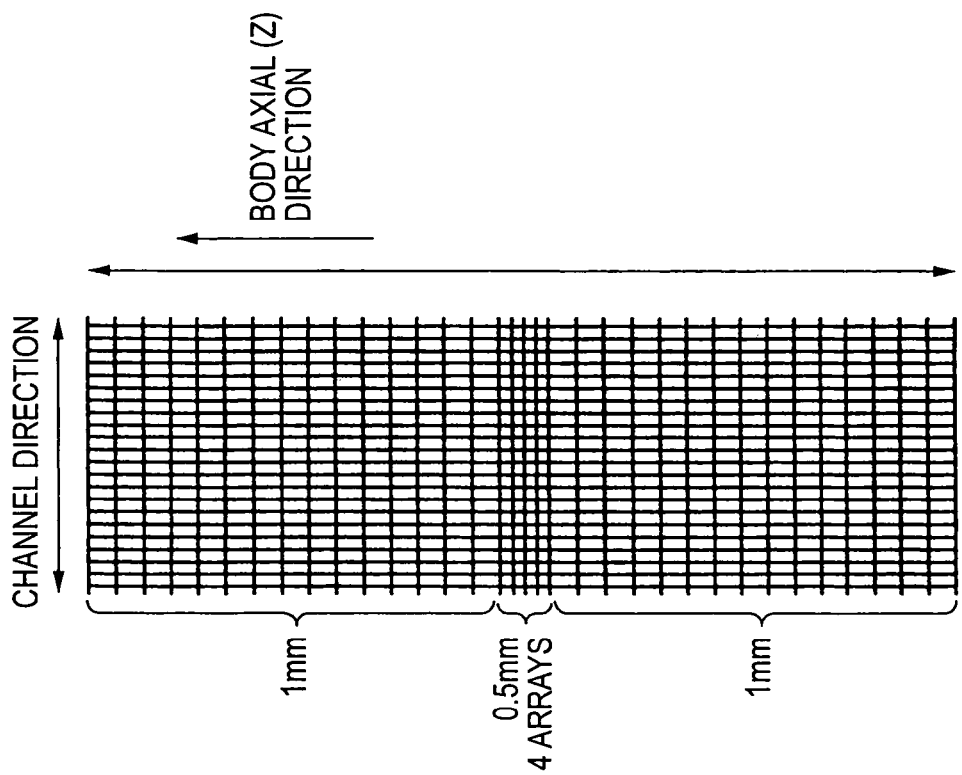
FIG. 3A and FIG. 3B are views showing part of a detecting plane of a 2-D detector system included in the X-ray CT apparatus.
Figure 3B:
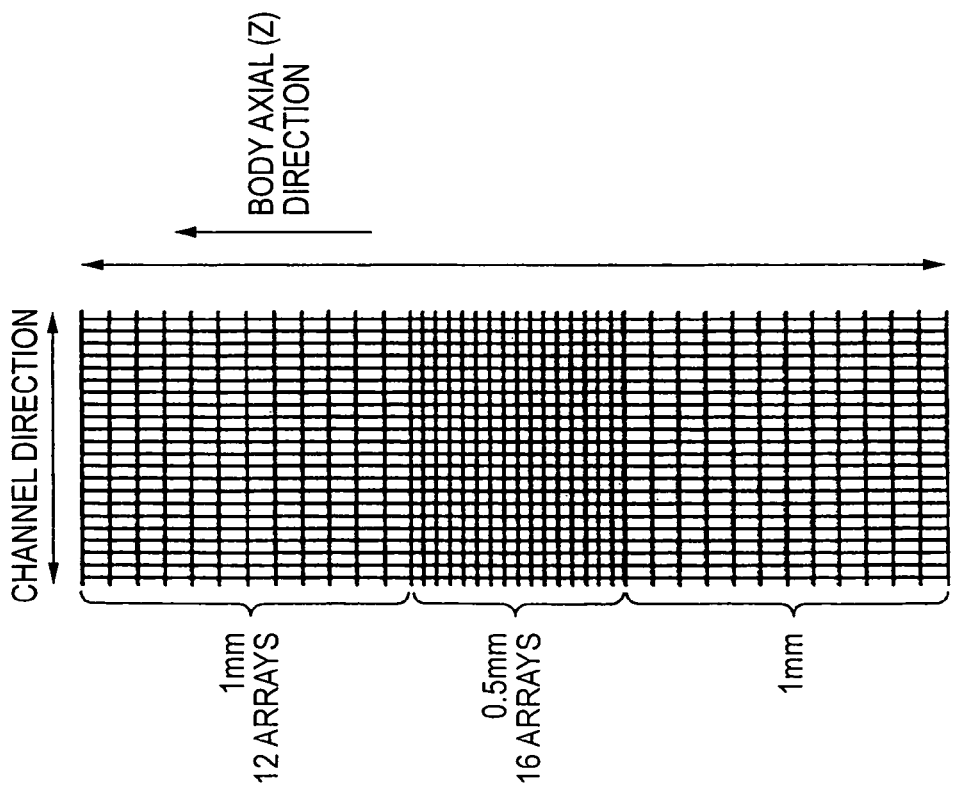

FIG. 3A and FIG. 3B are views showing. part of detecting planes of the 2-D detector systems 103. included in the X-ray CT apparatuses A and B, respectively. A width of the detecting plane in the body axial direction is equal in the both drawings. As shown in FIG. 3A, the X-ray CT apparatus A capable of photographing 4 arrays of tomographic layers simultaneously is provided with 4 detecting element arrays having the minimum slice width of 0.5 mm. On the other hand, as shown in FIG. 3B, the X-ray CT apparatus B capable of photographing 16 arrays of tomographic layers simultaneously is provided with 16 detecting element arrays having the minimum slice width of 0.5 mm.

As a method of converting an incident X-ray to electrical charges in the detecting element, a direct converting method and an indirect converting method are available. The direct converting method exploits generation of electron-hole pairs within a semiconductor by an X-ray and movement of electrons and holes to the electrodes, that is, a so-called photoelectric phenomenon. On the other hand, the indirect converting method is a method of converting an X-ray into light with the use of a fluorescent substance, such as a scintillator, and then the light is converted to electrical charges with the use of a photoelectric converting element, such as a photodiode. The X-ray detecting element used herein can adopt either method.

The data acquisition circuit (DAS) 104 includes a plurality of data acquisition element arrays in which DAS chips are aligned. A vast volume of data with respect to all the M×N channels detected in the 2-D detector system 103 (hereinafter, data of M×N channels per view is referred to as the raw data) is inputted into the DAS 104, and subjected to amplification processing, analog-to-digital conversion, etc., after which the data is transmitted collectively to a data processing unit on the stationary side via the not-contact data transmission device 105 through optical communications.

Between the DAS 104 and the 2-D detector system 103 is disposed a switch group used to switch connection states between the respective detecting elements and data acquisition element arrays. Respective switching control operations for the switch group are performed by the host controller 110 based on the scan conditions. In other words, the host controller 110 switches connection states between the respective detecting element arrays provided to the 2-D detector system 103 and the data acquisition elements by controlling the switch group, and puts X-ray transmission data detected in the respective detecting elements together in a certain unit. Then, X-ray transmission data of a plurality of slices that matches with the scan conditions is read out from the respective detecting elements to the DAS 104 in the latter stage, and is subjected to certain processing. Hereinafter, the number of the data acquisition element arrays used to read out data from the respective detecting elements is referred to as "the DAS array number". The maximum value of the DAS array number depends on the number of tomographic layers that can be photographed simultaneously in each X-ray CT apparatus. More specifically, because the X-ray CT apparatus A can photograph up to 4 arrays of tomographic layers simultaneously, 4 is given as the maximum DAS array number. On the other hand, because the X-ray CT apparatus B can photograph up to 16 arrays of photographic layers simultaneously, 16 is given as the maximum DAS array number. Also, by adequately controlling the switch group, the DAS array number of the X-ray CT apparatus B can be changed to 4 or 8.

The non-contact data transmission device 105 optically transmits the acquired X-ray transmission data to a device in the next stage. The non-contact data transmission device 105, the DAS 104, etc. are provided with the ability to perform ultra high-speed processing, so that a vast volume of 2-D projection data generated at a high speed in the 2-D detector system 103 can be transmitted without causing a time delay.

The pre-processing device 106 receives raw data from the DAS 104 via the non-contact data transmission device 105, and performs sensitivity correction and X-ray intensity correction. The raw data of 360° done with various corrections is temporarily stored into the storage device 111. The data done with the pre-processing in the pre-processing device 106 is referred to as "projection data".

The gantry driving portion 107 performs driving control, such as allowing the X-ray tube 101 and the 2-D detector system 103 to rotate integrally about the central axis, which is parallel to the body axial direction of a subject inserted into a diagnostic opening.

The high voltage transformer assembly 109 is a device to supply, via the slip ling 108, the X-ray tube 101 with power needed to irradiate an X-ray, and comprises a high voltage transformer, a filament heating converter, a rectifier, a high voltage switching device, etc. A high voltage from the high voltage transformer assembly 109 is supplied to the X-ray tube 101 by means of the slip ring 108.

The host controller 110 systematically performs control related to various kinds of processing, such as photographing processing, data processing, and image processing. For example, in the photographing processing, the host controller 110 stores the pre-input scan conditions, such as the slice width, into the internal memory, and controls the high voltage transformer assembly 109, an unillustrated diagnostic table driving portion, the gantry driving portion 107, a quantity and a rate of feeding of the diagnostic table in the body axial direction, a rotation rate and a rotation pitch of the X-ray tube 101 and the 2-D detector system 103, irradiation timing of an X-ray, etc. under the scan conditions chosen automatically from the patient ID or the like (or the scan conditions directly set from the input device 115 in a manual mode), and then performs photographing processing of an X-ray CT image by irradiating an X-ray cone beam or an X-ray fan beam from many directions with respect to a desired photographing region of a subject.

The host controller 110 also transmits raw data generated in the DAS 104 to the data managing system 15 at certain timing via the network communications device 119. Further, the host controller 110 receives raw data from the data managing system 15 at certain timing via the network communications device 119, and controls the reconstruction device 114 to perform fan beam reconstruction or cone beam reconstruction.

The storage device 111 stores image data including raw data, projection data, and tomographic data, as well as programs or the like used to make an examination plan.

The auxiliary storage device 112 is a device having a storage region of a capacity large enough to store reconstruction image data generated in the reconstruction device 114.

The reconstruction device 114 generates reconstruction image data of a certain number of slices by applying reconstruction processing to the projection data based on certain reconstruction parameters (a reconstruction region size, a reconstruction matrix size, an extraction threshold for a region of interest, etc.). Reconstruction processing generally includes cone beam reconstruction and fan beam reconstruction.

The cone beam reconstruction is the reconstruction using information as to a cone angle of an X-ray cone beam shaped by the collimator, and typical examples include the Feldkamp method, the ASSR method, etc.

The Feldkamp reconstruction method is an improved approximate reconstruction method based on the fan-beam convolution back-projection method with the aim of generating 3-D distribution data of X-ray absorption coefficients (hereinafter, referred to as volume data (a stereoscopic (3-D) set of plurality items of voxel data)) by handling a region to be processed wide in the slice direction A as a set of a plurality of voxels. In other words, in the Feldkamp reconstruction method, data, being deemed as fan projection data, is convoluted, and back projection is performed along an oblique ray corresponding to an actual cone angle with respect to the rotation central axis.

The ASSR method is a method of reconstructing an image by extracting and using approximate projection data of an X-ray path that approximates to the position of a virtual plane (more effectively, an oblique plane inclined with respect to the central axis of the helical scan) defined by 2-D projection data.

In each of the embodiments below, the Feldkamp reconstruction method is used as the cone beam reconstruction processing in order to provide a concrete description. According to this reconstruction, an error in the reconstruction processing can be reduced by applying at least one of two kinds of correction processing as follows.

First correction processing is to apply correction processing to an increase of a length along which an X-ray beam passes through a subject when the X-ray beam is incident obliquely on the reconstruction plane (slice plane). In other words, a beam path length that varies with the position of a cone beam X-ray in the body axial direction is corrected with respect to projection data (pre-processing may have been applied but is not necessarily applied) obtained in the data acquisition device.

Second correction processing is to correct an error, which is a displacement between an actually measured X-ray path and a computed X-ray path linking a focal point of an X-ray and the center of a voxel defined for convenience of reconstruction processing. In other words, according to the second correction processing, certain computation processing is applied to projection data (of the detecting element) actually measured along a plurality of X-ray paths (for example, 4 X-ray paths) that are actually present around a computed X-ray path, and the computation data thus obtained, being deemed as back projection data along a straight line indicated by the computed X-ray path, is assigned with a certain weight and back projected. In the case of helical scan, in particular, the positional relation between a desired reconstruction plane and the focal point of an X-ray varies with respect to the slice direction, and it is therefore preferable to change a detecting element array (data thereof) to be used in the computation processing or a degree of contribution of the detecting element array for each position of the focal point of an X-ray (or each view).

On the other hand, the fan beam reconstruction processing uses, for example, the fan-beam convolution back-projection method. In other words, an image is reconstructed based on projection data on the assumption that a ray intersects at right angles with the rotation central axis in the back projection (on the assumption that the projection data is obtained from an X-ray in a direction perpendicular to the body axial direction).

Which of these reconstruction methods is feasible in each X-ray CT apparatus depends on the maximum DAS array number of the X-ray CT apparatus. Also, when both of the reconstruction methods are feasible in the X-ray CT apparatus, which reconstruction method should be performed depends on the DAS array number related to the obtained raw data.

More specifically, the X-ray CT apparatus A given with 4 as the maximum DAS array number is able to scan 4 planes simultaneously. Hence, the reconstruction device 114 in the X-ray CT apparatus A having the maximum DAS array number of 4 is able to perform only the fan beam reconstruction. On the other hand, because the X-ray CT apparatus B has 16 detecting element arrays and is given with 16 as the maximum DAS array number, and is therefore able to scan 4, 8, or 16 planes simultaneously. Hence, the reconstruction device 114 included in the X-ray CT apparatus B is able to perform the fan beam reconstruction in the case of scanning 4 planes simultaneously, and the cone beam reconstruction in the case of scanning 8 or 16 planes simultaneously.

The input device 115 is a device including a keyboard, various kinds of switches, a mouse, etc., through which an operator is able to input various scan conditions, such as a slice thickness and the number of slices.

The image processing portion 118 applies image processing for display, such as window conversion and RGB processing, on reconstruction image data generated in the reconstruction device 114, and outputs the resulting data to the display device 116. Also, at a command from the operator, the image processing portion 118 generates a tomographic image on an arbitrary plane, a projection image from an arbitrary direction, and a so-called pseudo 3-D image, such as a 3-D surface rendering image, and outputs the images thus generated to the display device 116. The image data thus outputted is displayed on the display device 116 as an X-ray CT image.

The network communication device 119 transmits/receives raw data to/from the data managing system 15 via a network.

The data processing, such as reconstruction and multiplanar reconstruction, and a display operation are generally performed in the X-ray CT apparatus 10. However, another image processing apparatus may be provided in addition to the X-ray CT apparatus 10, and the foregoing processing and operation may be performed in this image processing apparatus. When another image processing apparatus is used as described above, data transmitted from the X-ray CT apparatus 10 does not impair the advantages of this embodiment in any state, that is, before reconstruction, after reconstruction, or immediately before being displayed after data processing.

(Data Managing System)

A configuration of the data managing system 15 will now be described. The data managing system 15 sequentially receives raw data from the X-ray CT apparatuses A and B via the network, and stores the raw data in its own DB (database). Also, the raw data thus received is backed up automatically, managed collectively according a management table created in the data managing system 15, and transmitted to the X-ray CT apparatus as needed.

Figure 4:
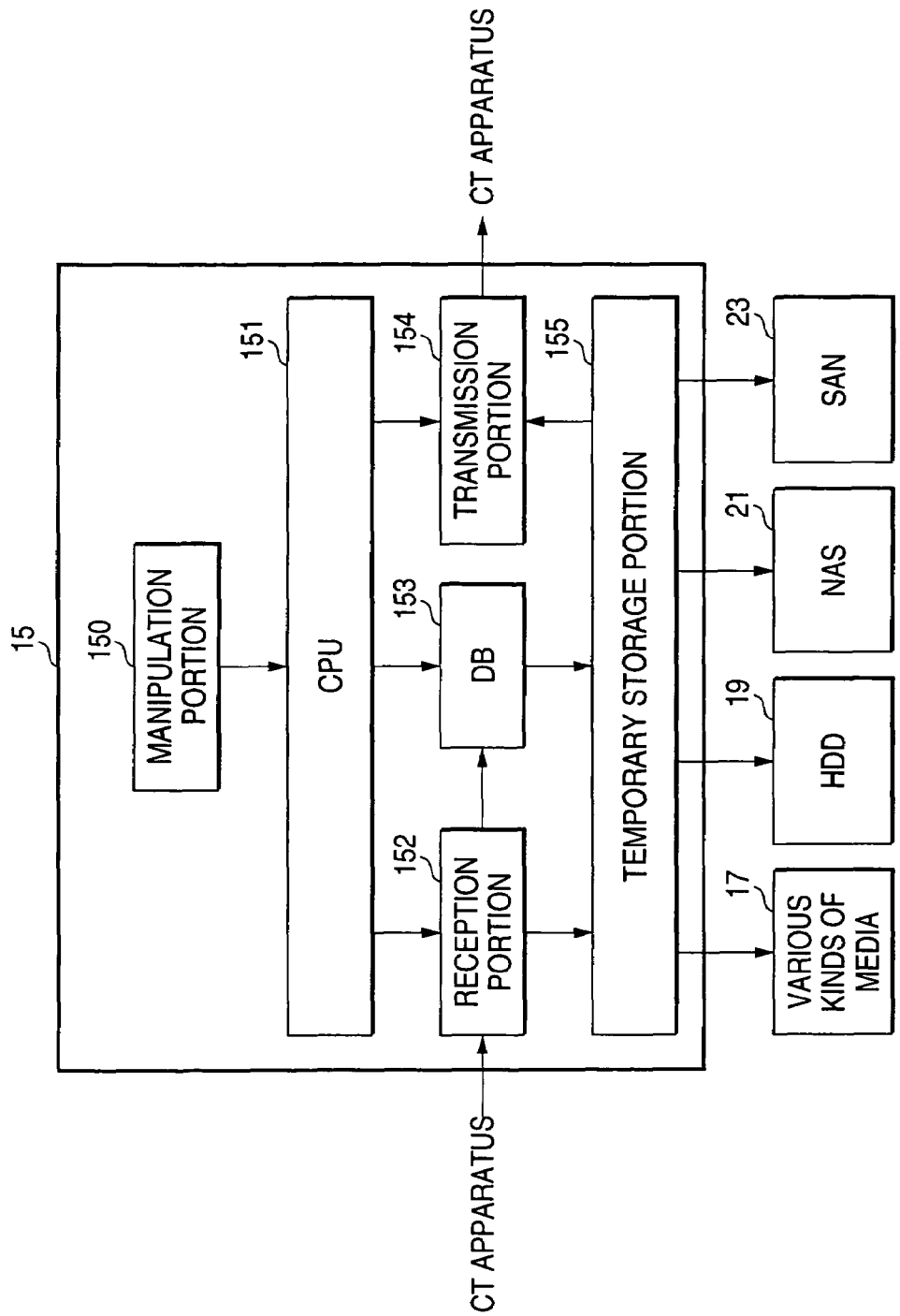
FIG. 4 is a block diagram showing a configuration of a data managing system.

As shown in FIG. 4, the data managing system 15 includes a manipulation portion 150, a CPU 151, a reception portion 152, a DB 153, a transmission portion 154, a temporary storage portion 155.

The manipulation portion 150 includes a device, such as a keyboard, various switches, and a mouse, through which the operator inputs a command.

The CPU 151 systematically performs control as to raw data management. For example, the CPU 151 stores raw data received at the reception device 152 into the DB 153, and transmits backup data to a certain storage device via the transmission portion 154. Also, the CPU 151 creates a management table described below based on the raw data and the appended information received from the respective X-ray CT apparatuses, and manages the raw data based on the management table. The appended information referred to herein means information including at least the data number, the name of a patient, the date of photographing, the DAS array number, the photographing slice width, etc.

The reception portion 152 receives, via the network, the raw data and appended information transmitted from the network communication device 119 installed in each X-ray CT apparatus 10.

The DB 153 stores the raw data and the appended information received at the reception portion 152, the management table created by the CPU 151, etc.

FIG. 5 is a view showing one example of the management table stored in the DB 153. As shown in the drawing, the raw data received at the reception portion 152 is managed based on the appended information.

The transmission portion 154 transmits raw data for data backup to respective storage devices via the network under the control of the CPU 151.

The temporary storage portion 155 temporarily stores raw data upon reception and transmission thereof.

(Storage Device)

The respective storage devices included in the system will now be described. Each storage device stores raw data and appended information obtained in any X-ray CT apparatus on the X-ray CT system for data backup. Which raw data should be backed up to which storage device is managed by the data managing system 15.

The various kinds of media 17 record raw data into removable recording media, such as a 4-mm DAT tape, a DLT tape, an AIT tape, and a DVD.

The HD 18 records raw data or the like into an equipped HD.

The NAS 21 includes a file system inside the storage main body, and can be constructed by directly using an existing network. The NAS 21 transfers all the data needed for processing over the network.

The SAN 23 is a high-speed storage device network system comprising storage device managing software of different kinds, an application server, and network hardware. Compared with the NAS 21, the SAN 23 is different in that sharing of information related to the management data is not allowed, a connection to the data managing system 15 is established by a fiber channel, etc.

(Photographing, Raw Data Management, and Reconstruction)

A series of operations by the X-ray CT system will now be described by explaining, by way of example, a case where the X-ray CT apparatus A performs helical scan, then the data managing system 15 manages the obtained raw data, and the X-ray CT apparatus B reconstructs the raw data. This is a case on the assumption that a radiographer photographs a patient A using the X-ray CT apparatus A, and the raw data is managed by the data managing system 15, while a physician B in another room reads out the raw data from the system 15 and reconstructs an image using the X-ray CT apparatus B in making an image diagnosis for the patient A.

Figure 6:
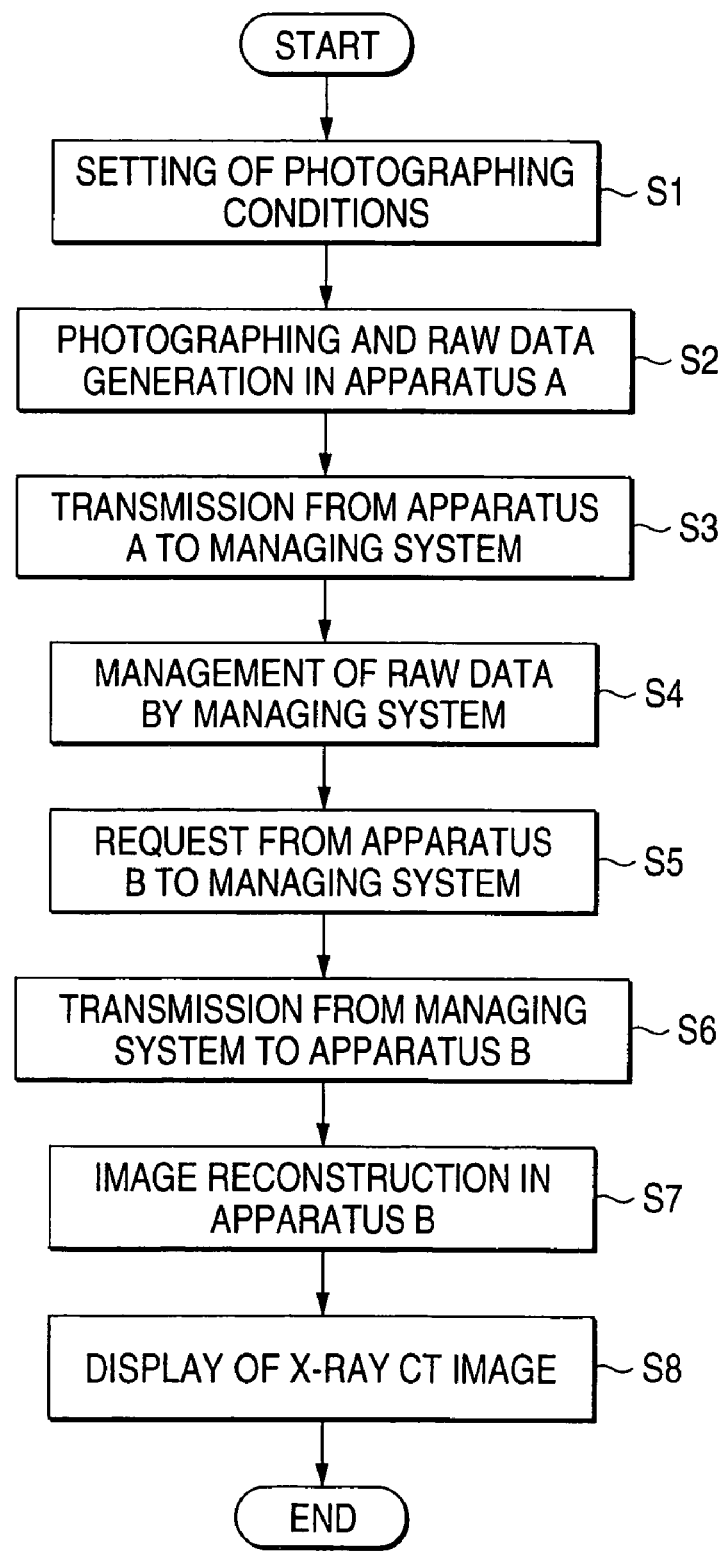
FIG. 6 is a flowchart detailing the processing procedure in a raw data managing operation according to a first embodiment.

FIG. 6 is a flowchart detailing the processing procedure in a raw data managing operation by the X-ray CT system. As shown in the drawing, the photographing conditions are set in the X-ray CT apparatus A (Step S1). More specifically, scanogram is generated by performing scano-photographing on a subject (patient A) laid on the table top of the diagnostic table to determine the start position of CT scan and the photographing conditions. Based on the scanogram, the operator sets the scan conditions (region to be examined, scan type (either the conventional scan or the helical scan is chosen), the range, start position, and end position of scan, the size of the field of view FOV, the photographing slice width (slice thickness×the number of slices), a volume size, an inclined angle of the gantry, a tube voltage, a tube current, a scan speed (a rotation rate of the X-ray tube and the detector), a quantity of movement of the diagnostic table while the X-ray tube rotates once, a quantity of movement of the diagnostic table, etc.). The scan conditions thus set are automatically loaded to the host controller 110. Herein, assume that, for example, 4 slices at a slice width of 1.0 mm are set as the photographing slice width (the photographing slice width: 1.0 mm×4 slices).

In order to choose the optimal combination of these conditions, not only considerable expert knowledge and experience are needed, but also a complicated work is involved. Hence, the conditions are generally set according to an operator assisting function (examination plan creating function) furnished to the X-ray CT apparatus.

Then, the X-ray CT apparatus A performs photographing under the photographing conditions thus set, and generates raw data (Step S2). More specifically, upon input of an examination start command from the operator, the table top is moved to immediately before the scan start position (run-up position of helical scan) while the rotation ring 102 starts to rotate. When the rotation ring 102 reaches a certain speed, the tube voltage and the tube current set as the scan conditions are supplied to the X-ray tube 101 from the high voltage transformer assembly 109, and the table top starts to slide in the body axial direction upon irradiation of an X-ray. It should be noted that the opening width of the collimator has been changed at this point to acquire data in the slice width being set. Helical scan is performed as the subject laid on the table top is moved in the body axial direction while the X-ray tube 101 keeps irradiating an X-ray while rotating about the subject.

The X-ray having passed through the subject is detected in the 2-D detector system 103, and raw data is generated in the DAS 104 based on the detection. The raw data thus generated is transmitted to the network communication device 119 via the non-contact data transmission device 105 (Step S3). The network communication device 119 then transmits the raw data to the data managing system 15 via the network.

The data managing system 15 subsequently performs management for the raw data and appended information received from the X-ray CT apparatus A (Step S4). More specifically, the data managing system 15 stores the received raw data into the DB 153, and creates the management table based on the appended information. The data managing system 15 also transfers the received raw data to a certain storage device (any one of various kinds of media 17, HD 19, NAS 21, and SAN 23) to back up the data, and registers the device to which the data is backed up in the management table in the DB 153. Which of the various kinds of media 17, the HD 19, the NAS 21, and the SAN 23 should be chosen as the storage device depends on the settings; however, the settings can be changed as needed with an input from the manipulation portion 150.

Then, the X-ray CT apparatus B transmits a request to the data managing system 15 via the network for the raw data related to the patient A (data assigned with the management number 012345 in FIG. 4) (Step S5). Upon receipt of the request, the data managing system 15 reads out the raw data and the appended information related to the patient A from the DB 153, and transmits the same to the X-ray CT apparatus B from the transmission portion 154 (Step S6).

The X-ray CT apparatus B then performs pre-processing on the raw data related to the patient A thus received, and thereby generates 2-D projection data. Subsequently, the X-ray CT apparatus B applies helical interpolation to the 2-D projection data, and performs image reconstruction (Step S7). The image reconstruction is performed as specified below based on the DAS array number as the appended information. That is, given 4 as the DAS array number for the received raw data related to the patient A, the reconstruction device 114 in the X-ray CT apparatus B generates an X-ray CT image by performing fan beam reconstruction according to certain reconstruction parameters.

The X-ray CT image thus generated is displayed on the display device 116 in a certain form (Step S8). Further, By applying certain image processing to the reconstructed image in the image processing portion 118, it is possible to display a tomographic image on an arbitrary plane, a projection image from an arbitrary direction, and a so-called pseudo 3-D image, such as a 3-D surface rendering image of a specific organ through rendering processing.

The above description described a case where the X-ray CT apparatus A performs photographing at the photographing slice width of 1.0 mm×4 slices, then the data managing system 15 manages the obtained raw data, and the X-ray CT apparatus B receives the raw data and performs the fan beam reconstruction. Contrary to this, in a case where the X-ray CT apparatus B reads out raw data obtained, for example, by an X-ray CT apparatus C (not shown) capable of detecting 8 arrays of tomographic layers simultaneously (for example, the photographing slice width: 0.5 mm×8 slices, DAS array number: 8) from the data managing system 15 and performs reconstruction therein, the X-ray CT apparatus B performs cone beam reconstruction. The X-ray CT apparatus B is also able to generate an image through fan beam reconstruction processing by putting the raw data received from the data managing system 15 in a unit of two arrays and thereby generating raw data with a photographing slice width of 1.0 mm×4 slices.

It may be configured in such a manner that when a raw data request is transmitted to the data managing system 15 in Step S5, the request-sender X-ray CT apparatus requests only the raw data judged as being reconstructible therein. For example, the unillustrated X-ray CT apparatus C capable of detecting 8 arrays of tomographic layers simultaneously is not able to reconstruct the raw data assigned with the management number 012787 in FIG. 5 with 16 being given as the DAS array number. In such a case, when the request-sender X-ray CT apparatus C judges that the raw data is of no use, the X-ray CT apparatus C may not receive the raw data assigned with the management number 012787 from the data managing system 15.

According to the configurations described above, the advantages as follows can be achieved.

In this embodiment, the raw data obtained in the X-ray CT apparatus A is transmitted at a high speed to the data managing system 15 without being stored in the storage device 111 installed in the X-ray CT apparatus A. This can omit a time needed to record the raw data into the storage device 111 in the X-ray CT apparatus A, which in turn makes it possible to improve the efficiency of a diagnostic work. In addition, because the raw data thus transmitted is managed collectively in the DB 153 in the data managing system 15, searches or the like can be performed efficiently.

Also, in this embodiment, the raw data transferred to the data managing system 15 is automatically stored into the DB 153 having a larger memory capacity than the storage device 111, and is also stored automatically into another storage device for data backup. Hence, even when a vast volume of data has to be stored in the case of multi-slice method or the like, the entire raw data can be stored rapidly.

In addition, the data managing system 15 manages which raw data has been backed up to which storage device. Hence, even when more than one item of raw data is distributed and stored in various backup storage devices, desired raw data can be retrieved rapidly. Further, unlike the conventional cases, it is no longer necessary to manage the acquired raw data in a DVD, a DAT tape, a DLT tape, or an AIT tape through human-based operations, which makes it possible to improve the efficiency of management markedly. The raw data obtained through photographing is managed as the diagnostic information in the past, and will be used in a future diagnosis. The managing function described herein is particularly advantageous when a vast volume of raw data has to be managed as in the case described above.

The raw data managed collectively in the data managing system 15 is transmitted to the X-ray CT apparatus B at a request. The X-ray CT apparatus B performs the fan beam reconstruction or the cone beam reconstruction depending on the DAS array number. This allows the X-ray CT apparatus A to continue the photographing work without having to spare a time for reconstruction processing. Moreover, any X-ray CT apparatus is able to obtain raw data from the data managing system 15 at arbitrary timing, and enables an X-ray CT image to be observed through image reconstruction. As a result, a series of works from the photographing to image reconstruction to a diagnosis based on an X-ray CT image can be distributed to a plurality of X-ray CT apparatuses, which makes it possible to improve the efficiency and increase a degree of freedom of a diagnostic work.

Second Embodiment

A second embodiment will now be described. The second embodiment is a case on the assumption that a radiographer photographs a patient B using the X-ray CT apparatus B, and the obtained raw data is managed by the data managing system 15, while the raw data is automatically transmitted from the data managing system 15 to the X-ray CT apparatus A installed in another room for an image diagnosis to be made for the patient B.

In this case, the DAS array information for the respective X-ray CT apparatuses has been set in the data managing system 15, and according to this information, the data managing system 15 transmits only reconstructible raw data to the respective X-ray CT apparatuses.

Figure 7:
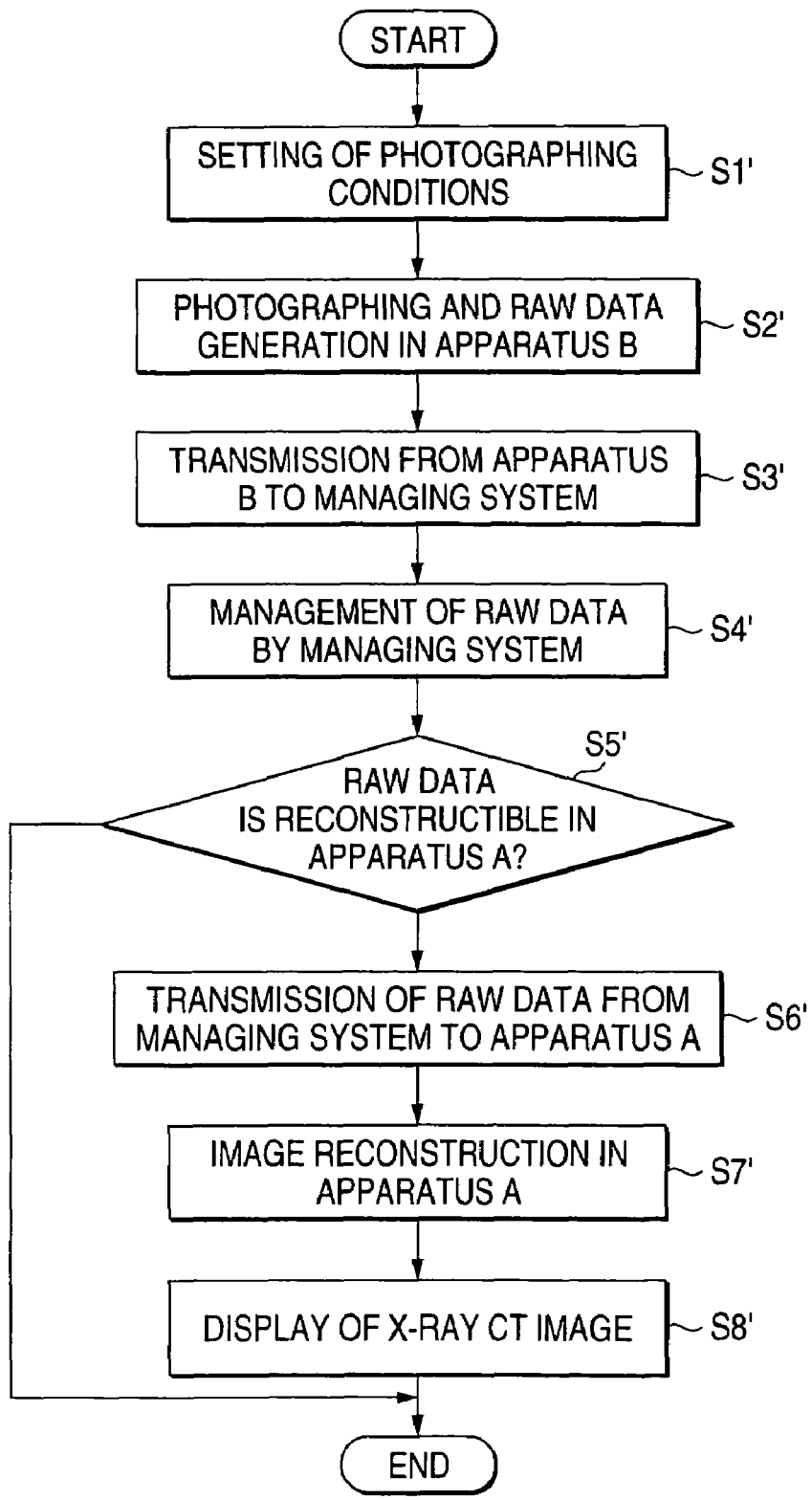
FIG. 7 is a flowchart detailing the processing procedure in a raw data managing operation according to a second embodiment.

FIG. 7 is a flowchart showing the processing procedure in a raw data managing operation by the X-ray CT system. As shown in the drawing, the photographing operation by the X-ray CT apparatus B (Steps S1' and S2'), transmission to the data managing system 15 (Step S3'), and the raw data managing operation in the system 15 (Step S4') are identical with their counterparts in the first embodiment above, and an explanation is not repeated.

The data managing system 15 judges whether the raw data received from the X-ray CT apparatus B is reconstructible in the X-ray CT apparatus A, based on the management table stored in the DB 153 and a reconstruction table indicating the data processing capability of the reconstruction device (reconstruction engine) equipped to each X-ray CT apparatus on the network (Step S5').

FIG. 8 is a view showing one example of the reconstruction table related to the X-ray CT apparatus A and stored in the DB 153. In the drawing, a blank circle, ○, indicates that adequate reconstruction is possible, and a cross, X, indicates that adequate reconstruction is impossible. For example, given 0.5 mm×4 slices as the photographing slice width and 4 as the DAS array number of the raw data obtained in the X-ray CT apparatus B. Then, fan beam reconstruction has to be applied to the raw data in this case. According to the reconstruction table of FIG. 8, the X-ray CT apparatus A is able to perform fan beam reconstruction. In view of the foregoing, the CPU 151 in the data managing system 15 judges that the raw data in question is reconstructible in the X-ray CT apparatus A.

On the other hand, given 0.5 mm×16 slices as the photographing slice width and 16 as the DAS array number of the raw data obtained in the X-ray CT apparatus B. Then, cone beam reconstruction has to be applied to the raw data. According to the reconstruction table shown in FIG. 8, however, the X-ray CT apparatus A is adaptable only to fan beam reconstruction, and is not able to perform cone beam reconstruction. In view of the foregoing, the CPU 151 in the data managing system 15 judges that the data in question is not reconstructible in the X-ray CT apparatus A. When the raw data is judged as being not reconstructible in this manner, it is preferable that the transmission portion 154 in the data managing system 15 does not transmit the raw data to the X-ray CT apparatus A.

When the raw data is judged as being reconstructible in Step S5', the data managing system 15 transmits the raw data to the X-ray CT apparatus A at certain timing by means of the transmission portion 154 (Step S6'). The X-ray CT apparatus A then applies pre-processing to the raw data related to the patient A thus received, and thereby generates 2-D projection data. Subsequently, the X-ray CT apparatus A applies helical interpolation to the 2-D projection data, and performs fan beam image reconstruction (Step S7').

The X-ray CT image thus generated is displayed on the display device 116 in a certain form (Step S8'). Further, by applying certain image processing to a reconstructed image in the image processing portion 118, it is possible to display a tomographic image on an arbitrary plane, a pseudo 3-D image, etc.

In Step S5', the data managing system 15 makes a judgment based on the management table and the reconstruction table stored in the DB 153. Contrary to this, it may be configured in such a manner that the data managing system 15 transmits an inquiry to the X-ray CT apparatus at the receiver's end, asking whether the raw data to be transmitted is reconstructible therein, and allows the X-ray CT apparatus at the receiver's end to judge whether the raw data is reconstructible therein.

As has been described, the same advantages as those achieved in the first embodiment can be achieved by the configuration of this embodiment. Also, because the reconstructible raw data is selectively transmitted by the data managing system 15, a human-based work can be reduced, which in turn makes it possible to improve the efficiency of a diagnostic work.

Third Embodiment

A third embodiment will now be described. In the third embodiment, the data managing system 15 is furnished with, in addition to the judging function described in the second embodiment, a function of processing raw data to meet the ability of the reconstruction engine at the receiver's end. More specifically, the data managing system 15 compares the DAS array number related to the raw data to be transmitted with the ability of the reconstruction engine equipped to the X-ray CT apparatus at the receiver's end. Upon judging from the comparison that the raw data cannot be reconstructed directly, the data managing system 15 performs reconstruction processing and transmits the reconstruction image data thus obtained to the X-ray CT apparatus, or processes the raw data to the level at or above which it becomes reconstructible in the X-ray CT apparatus at the receiver's end.

Figure 9:
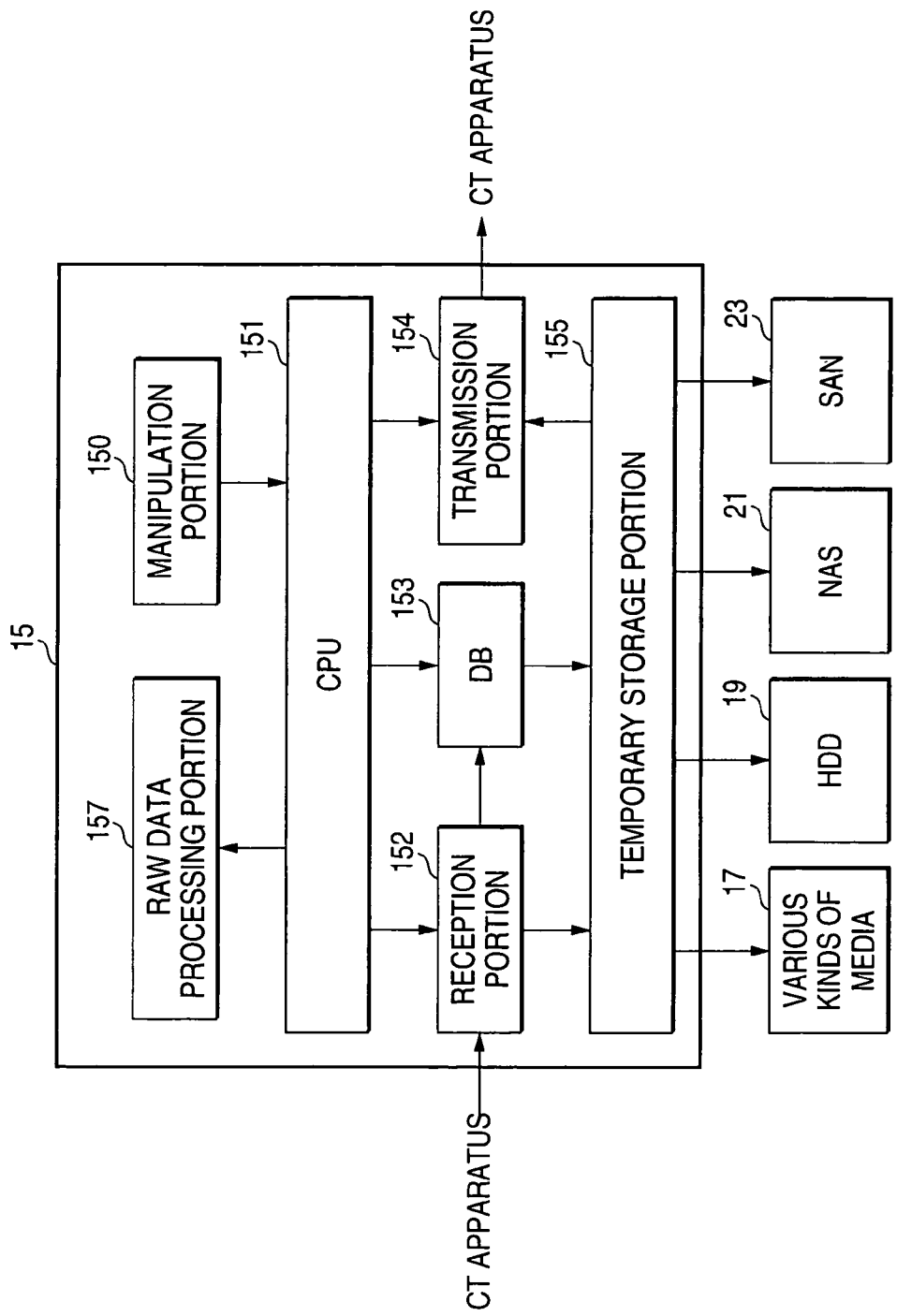
FIG. 9 is a block diagram showing a configuration of a data managing system according to a third embodiment.

FIG. 9 is a block diagram of the data managing system 15 according to this embodiment. As can be understood from comparison with FIG. 4, the difference is that the data managing system 15 further includes a raw data processing portion 157. The raw data processing portion 157 is furnished with a reconstruction engine function having a spec as high as or higher than the spec of the reconstruction engines equipped to the respective X-ray CT apparatuses linked to the network. Due to the upward compatibility of the reconstruction engine, this enables raw data processing described below to be performed in any of the X-ray CT apparatuses on the network upon receipt of raw data or the like.

Figure 10:
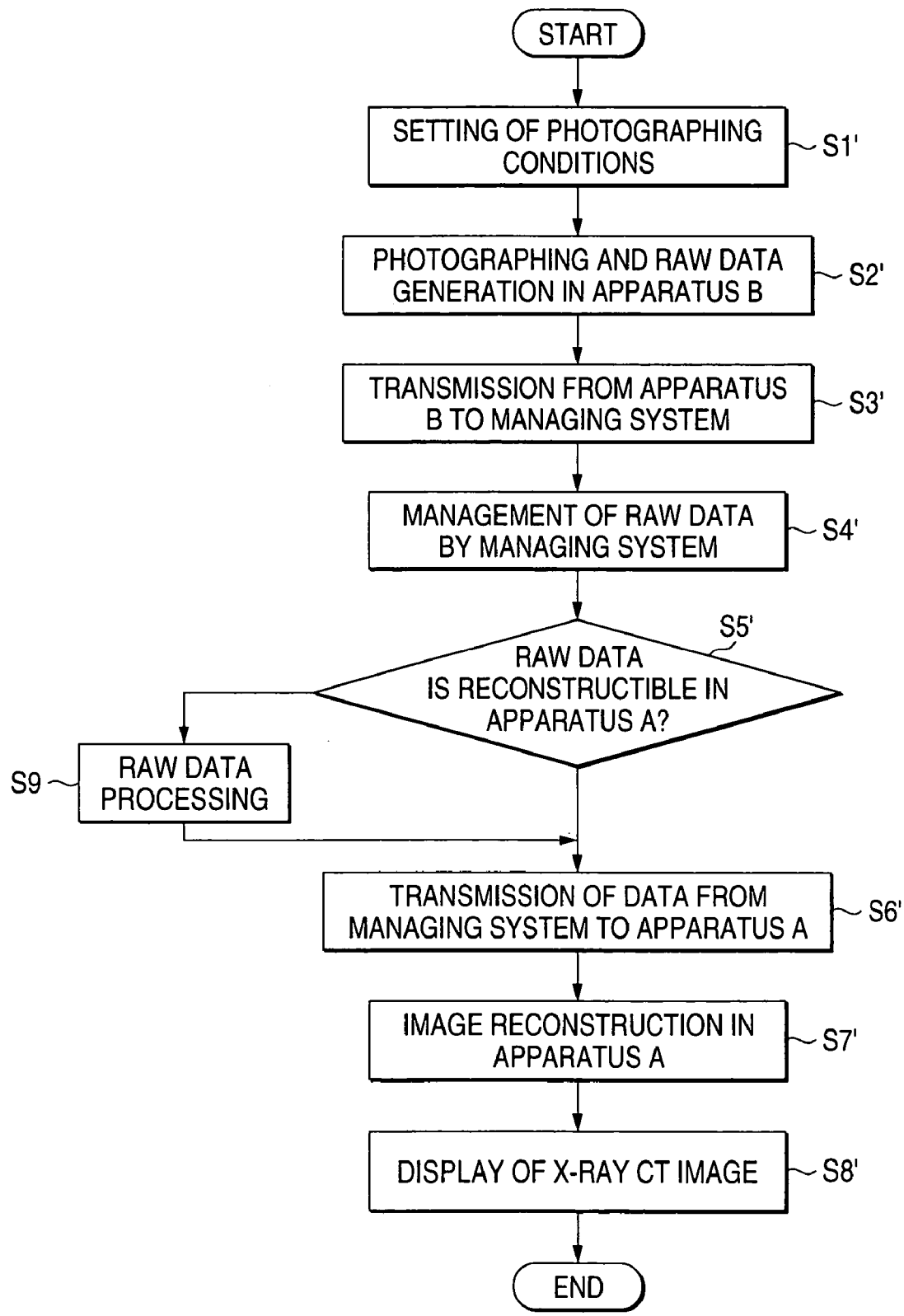
FIG. 10 is a flowchart detailing the processing procedure in a raw data managing operation by an X-ray CT system according to the third embodiment.

FIG. 10 is a flowchart detailing the processing procedure in a raw data managing operation by the X-ray CT system. When compared with FIG. 7, the flowchart in this embodiment is different from the flowchart in FIG. 7 in the processing performed after raw data is judged as being not reconstructible in Step 5'. Hence, hereinafter, processing performed after raw data is judged as being not reconstructible in Step 5' will be described step by step with reference to FIG. 10.

Referring to FIG. 10, the data managing system 15 judges whether the raw data received from the X-ray CT apparatus B is reconstructible in the X-ray CT apparatus A, based on the management table and the reconstruction table stored in the DB 153 (Step S5'). For example, given the data assigned with the management number 012566 of FIG. 5 (photographing slice width: 0.5 mm×8 slices, DAS array number: 8) as the raw data obtained in the X-ray CT apparatus B. Then, as shown in FIG. 8, because the X-ray CT apparatus A is adaptable only to fan beam reconstruction, the reconstruction engine equipped to the X-ray CT apparatus A is not able to adequately reconstruct the raw data having the photographing slice with of 0.5 mm×8 slices and DAS array number of 8. The CPU 151 therefore judges that the raw data assigned with the management number 012566 is not reconstructible in the X-ray CT apparatus A.

When the CPU 151 judges the raw data as being not reconstructible in Step S5', the raw data processing portion 157 starts to process the raw data assigned with the management number 012787 to be in a form reproducible into an X-ray CT image A in the X-ray CT apparatus A, with reference to the reconstruction table shown in FIG. 8 (Step S9). Herein, "to be in the form reproducible into an X-ray CT image A" means that the raw data assigned with the management number 012787 is reconstructed into reconstruction image data that can be reproduced as an X-ray CT image in the X-ray CT apparatus A, or the raw data having the photographing slice with of 0.5 mm×8 slices and DAS array number of 8 is put together in a unit of two arrays to generate raw data having the photographing slice width of 1.0 mm×4 slices, so that the X-ray CT apparatus A is able to perform image reconstruction adequately, etc.

The raw data (or reconstruction image data) processed in the raw data processing portion 157 is transmitted to the X-ray CT apparatus A at certain timing by means of the transmission portion 154 (Step S6'). Upon receipt of the raw data, the X-ray CT apparatus A performs pre-processing as needed and thereby generates 2-D projection data. Subsequently, the X-ray CT apparatus A applies helical interpolation to the 2-D projection data, and performs fan beam image reconstruction (Step S7'). Upon receipt of the reconstruction image data, the X-ray CT apparatus A skips the processing in Step S7' and proceeds to Step S8'.

An X-ray CT image obtained through the respective steps described above is displayed on the display device 116 in a certain form (Step S8'). Further, by applying certain image processing to a reconstructed image in the image processing portion 118, it is possible to display a tomographic image on an arbitrary plane, a pseudo 3-D image, etc.

In this embodiment, too, it may be configured in such a manner that, as has been described in the second embodiment, the data managing system 15 transmits an inquiry to the X-ray CT apparatus A at the receiver's end in step S5', asking whether the raw data to be transmitted is reconstructible therein, and allows the X-ray CT apparatus A at the receiver's end to judge whether the raw data is reconstructible therein. In this case, it may be further configured in such a manner that, upon judging the data as being not reconstructible, the X-ray CT apparatus A at the receiver's end requests the data managing system 15 to process the raw data.

While the present invention has been described in connection with the embodiments, modifications and alternations may occur to anyone skilled in the art without departing from the inventive concepts of the present invention, and it is to be understood that such modifications and alternations are within the scope of the present invention. For example, modifications as set forth in (1) and (2) below can be achieved without changing the subject matter of the present invention.

(1) In each of the embodiments above, the data managing system 15 is configured to manage the raw data and the appended information related to the raw data. Contrary to this, the similar advantages can be achieved even when the data managing system 15 is configured to manage projection data and appended information related to the projection data.

Figure 11:
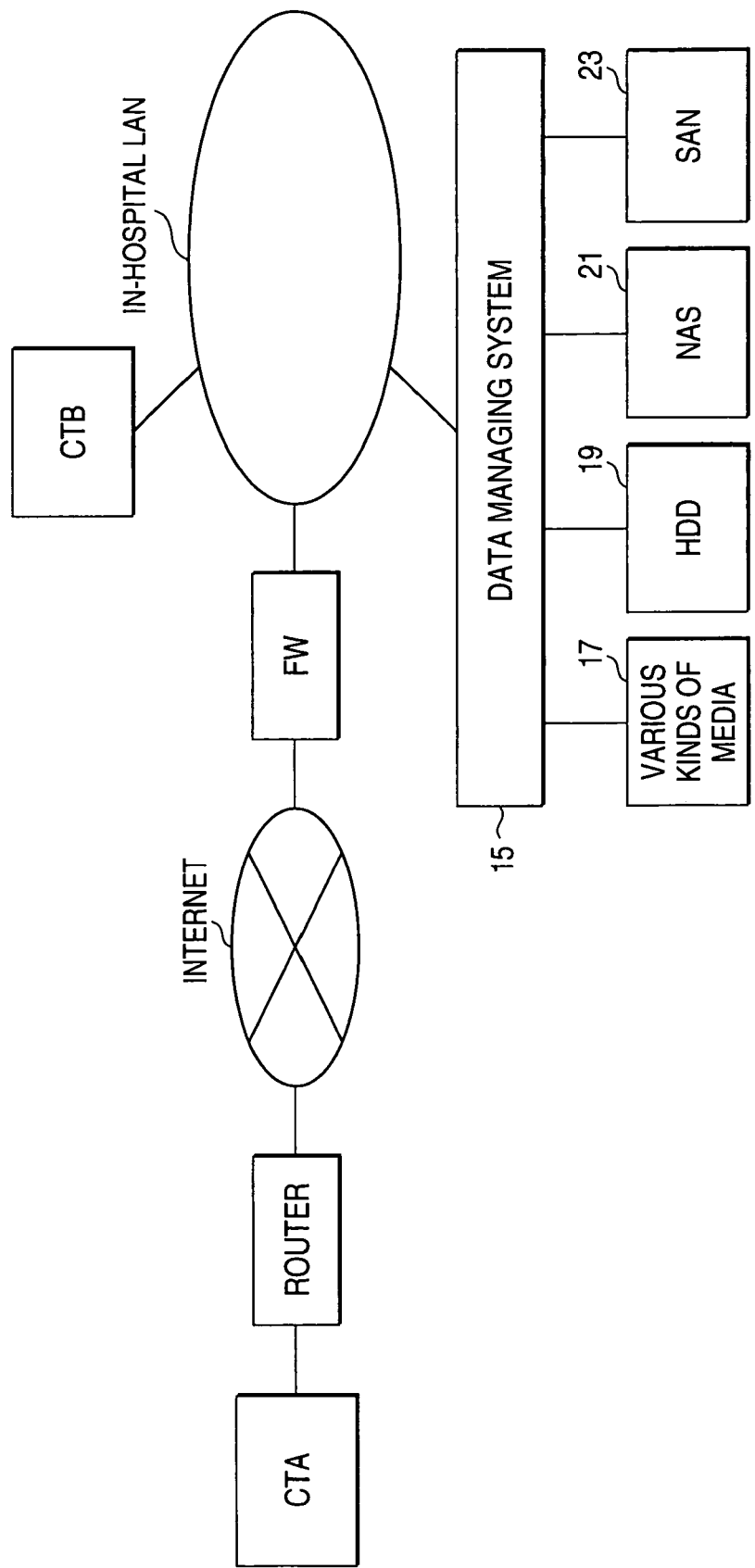
FIG. 11 is a view showing a modification of the first and second embodiments.

(2) In each of the embodiments above, explanations were given on the assumption that the X-ray CT system 10 is introduced into a closed facility like an in-hospital LAN. However, the present invention is not limited to such a case, and for example, as shown in FIG. 11, the present invention is adaptable to environments where the X-ray CT apparatus A is installed outside the hospital with the use of the Internet or the like. In this case, it is preferable to set a fire wall FW or the like to allow particular users alone to make an access.

(3) In each of the embodiments above, the data managing system 15 may be configured to confirm the state of an X-ray CT apparatus at the receiver's end from time to time, so that it transmits the raw data and the appended information only when the X-ray CT apparatus is in a reception enabled state (for example, when operations of the host controller are not occupied by photographing or the like). This can be achieved, for example, by making the respective X-ray CT apparatuses transmit information related to a current status to the data managing system 15 periodically, or by making the data managing system 15 confirm a current status of the respective X-ray CT apparatuses periodically. This configuration makes it possible to improve the efficiency in data communications.

The respective embodiments can be combined as needed when possible, and combined advantages can be achieved in such a case. Further, the embodiments described above include inventions at various stages, and a variety of inventions can be extracted by adequately combining a plurality of components disclosed above. For example, of all the components shown in the embodiments above, even when some components are omitted, while the object discussed in the "Problems that the present invention is to Solve" column can be achieved, and at least one of the advantages described in the "Advantage of the present invention" column is achieved, the arrangement that omits some components can be extracted as an invention.

According to the embodiments described above, it is possible to achieve a data managing system, an X-ray CT apparatus, and an X-ray CT system capable of improving the efficiency of a diagnostic work by efficiently managing a vast volume of data obtained through photographing.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scopes of the general inventive concept as defined by the appended claims and their equivalents.

What is claimed is:

1. An X-ray computed tomographic system, comprising:
a first X-ray computed tomography apparatus;
a second X-ray computed tomography apparatus; and
a data managing system connected to said first and second X-ray computed tomography apparatuses via a network,
wherein said first X-ray computed tomography apparatus includes
an X-ray irradiating unit configured to irradiate an X-ray to a subject while rotating about the subject;
an X-ray detecting unit having a plurality of detecting element arrays aligned in a slice direction, in each of which a plurality of detecting elements, each generating electrical charges based on an incident X-ray, are aligned in a channel direction;
a data acquisition unit, having a plurality of data acquisition element arrays, configured to read out the electrical charges from said plurality of detecting elements by using a certain number of data acquisition element arrays among said plurality of data acquisition element arrays and to generate raw data or projection data based on the electrical charges; and
a first transmission unit configured to transmit, via said network to said data managing system, said raw data or projection data and appended information including the number of data acquisition element arrays used when reading out the electrical charges,
said data managing system includes
a first reception unit configured to receive said raw data or projection data and said appended information;
a storage unit configured to store said raw data or projection data and said appended information received;
a determining unit configured to determine, based on said appended information, whether image reconstruction by using one of said raw data and said projection data is possible in said second X-ray computed tomography apparatus; and
a second transmission unit configured to transmit one of said raw data and said projection data, and said appended information to said second X-ray computed tomography apparatus when said determining unit determines that reconstruction is possible, and
said second X-ray computed tomography apparatus includes
a second reception unit configured to receive said raw data or projection data and said appended information; and
a reconstruction unit configured to perform image reconstruction based on said raw data or projection data and said appended information received.

2. The X-ray computed tomographic system according to claim 1, wherein said reconstruction unit chooses, based on the number of arrays used, one of a first reconstruction method that does not concern an influence of a cone angle of an X-ray irradiated from said X-ray irradiating unit and a second reconstruction method that concerns the influence of the cone angle of the X-ray, and performs image reconstruction using the reconstruction method chosen.

3. The X-ray computed tomographic system according to claim 1, wherein said reconstruction unit chooses said first reconstruction method when 4 is given as said certain number, and said second reconstruction method when one of 8 and 16 is given as said certain number.

4. The X-ray computed tomographic system according to claim 1, wherein said data managing system further includes a backup data generating unit configured to generate backup data in a certain storage unit, based on said raw data or projection data and said appended information.

5. The X-ray computed tomographic system according to claim 4, wherein:
said data managing system further includes a table generating unit configured to generate a table that correlates said raw data or projection data and said appended information with the storage unit in which said backup data has been generated; and
said storage unit stores said table.

6. A data managing system connected to a first X-ray computed tomography apparatus and a second X-ray computed tomography apparatus via a network, said data managing system comprising:
a reception unit configured to receive, from said first X-ray computed tomography apparatus, one of raw data and projection data obtained in said first X-ray computed tomography apparatus and appended information including the number of data acquisition element arrays used when obtaining one of said raw data and said projection data;
a storage unit configured to store one of said raw data and said projection data, and said appended information received;
a determining unit configured to determine, based on said appended information, whether image reconstruction based on one of said raw data and said projection data is possible in said second X-ray computed tomography apparatus; and
a transmission unit configured to transmit one of said raw data and said projection data, and said appended information to said second X-ray computed tomography apparatus when said determining unit determines that reconstruction is possible.

7. The data managing system according to claim 6, further comprising a backup data generating unit to generate backup data in a certain storage unit, based on said raw data or said projection data and said appended information.

8. The data managing system according to claim 6, further comprising:
a data processing unit configured to process one of said raw data and said projection data to generate and display a reconstruction image in said second X-ray computed tomography apparatus when said determining unit determines that the reconstruction is impossible,
wherein said transmission unit transmits said appended information and the reconstruction image to said second X-ray computed tomography apparatus when said determining unit determines that reconstruction is impossible.

9. The data managing system according to claim 6, further comprising:
   a table generating unit configured to generate a table that correlates one of said raw data and said projection data, and said appended information with the storage unit in which said backup data has been generated,
   wherein said storage unit stores said table.

10. An X-ray computed tomography apparatus connected, via a network, to a data managing system, said apparatus comprising:
   a reception unit configured to receive, from said data managing system, one of raw data and projection data obtained in an X-ray computed tomography apparatus, and appended information including the number of data acquisition element arrays used when obtaining one of said raw data and said projection data;
   a reconstruction unit configured to perform image reconstruction based on one of said raw data and said projection data, and said appended information received; and
   a determining unit configured to determine whether one of said raw data and said projection data transmitted from said data managing system is reconstructible in said reconstruction unit;
   wherein said reception unit receives one of said raw data and said projection data, and said appended information only when said determining unit determines that reconstruction is possible.

11. The X-ray computed tomography apparatus according to claim 10, wherein said reconstruction unit chooses, based on the number of arrays used, one of a first reconstruction method that does not concern an influence of a cone angle of an X-ray irradiated from said X-ray irradiating unit and a second reconstruction method that concerns the influence of the cone angle of the X-ray, and performs image reconstruction using the reconstruction method chosen.

12. The X-ray computed tomography apparatus according to claim 10, wherein said reconstruction unit chooses said first reconstruction method when 4 is given as the number of data acquisition element arrays used, and said second reconstruction method when one of 8 and 16 is given as said certain number.

13. An X-ray computed tomographic system, comprising:
an X-ray computed tomography apparatus; and
a data managing system connected to said X-ray computed tomography apparatus via a network, wherein said X-ray computed tomography apparatus includes
   an X-ray irradiating unit configured to irradiate an X-ray to a subject while rotating about the subject;
   an X-ray detecting unit having a plurality of detecting element arrays aligned in a slice direction, in each of which a plurality of detecting elements, each generating electrical charges based on an incident X-ray, are aligned in a channel direction;
   a data acquisition unit, having a plurality of data acquisition element arrays, configured to read out the electrical charges from said plurality of detecting elements by using a certain number of data acquisition element arrays among said plurality of data acquisition element arrays and to generate raw data or projection data based on the electrical charges;
   a first transmission unit configured to transmit, via said network to said data managing system, said raw data or projection data and appended information including the number of data acquisition element arrays used when reading out the electrical charges;
   a first reception unit configured to receive said raw data or projection data and said appended information; and
   a reconstruction unit configured to perform image reconstruction based on said raw data or projection data and said appended information received, and
said data managing system includes
   a second reception unit configured to receive said raw data or projection data and said appended information;
   a storage unit configured to store said raw data or projection data and said appended information received;
   a determining unit configured to determine, based on said appended information, whether image reconstruction by using one of said raw data and said projection data is possible in said X-ray computed tomography apparatus; and
   a second transmission unit configured to transmit one of said raw data and said projection data, and said appended information to said X-ray computed tomography apparatus when said determining unit determines that reconstruction is possible.

* * * * *